United States Patent [19]

Suzuki

[11] Patent Number: 4,981,464

[45] Date of Patent: Jan. 1, 1991

[54] PLUG DEVICE FOR A TRANSFUSIBLE FLUID CONTAINER

[76] Inventor: Issei Suzuki, 3211-17 Fukami, Yamato-shi, Kanagawa-ken, Japan

[21] Appl. No.: 262,840

[22] Filed: Oct. 26, 1988

[30] Foreign Application Priority Data

Oct. 30, 1987 [JP] Japan ............................... 62-275107
Oct. 21, 1988 [JP] Japan ............................... 63-263844

[51] Int. Cl.[5] ............................................... A61M 5/32

[52] U.S. Cl. .................................... 604/415; 604/405; 604/411

[58] Field of Search ............... 604/405, 411, 414, 415, 604/251, 257; 215/247, 248, 249, 308, 309

[56] References Cited

U.S. PATENT DOCUMENTS 2,148,196 1/1937 Falk ................................ 215/309 X
2,438,149 3/1948 Cutter et al. ........................ 215/247
2,442,983 6/1948 Nesset ................................ 215/247
2,747,756 5/1956 Hartop, Jr. et al. ................ 215/247
2,817,372 12/1957 Barr, Sr. et al. ................ 604/411 X
4,232,095 11/1980 Safianoff ............................ 215/232
4,262,671 4/1981 Kersten ........................... 604/411 X

*Primary Examiner*—Robert A. Hafer
*Assistant Examiner*—Lynda Cofsky
*Attorney, Agent, or Firm*—Larson and Taylor

[57] ABSTRACT

A plug device for a transfusion container comprising a plug body made of rubber having an air passing portion into which a water repellent but air-permeable filter of porous material is inserted, a sealing sheet adapted to cover at least the surface portion of the rubber plug body which may be contacted with the transfusible fluid in the container, and a funnel shape air guide member which is formed integrally with the sealing sheet and the upper end of which is extended toward the bottom of the container.

20 Claims, 3 Drawing Sheets

PLUG DEVICE FOR A TRANSFUSIBLE FLUID CONTAINER

FIELD OF THE INVENTION

The present invention relates to a plug device for a transfusion fluid container Which may be used for infusing fluids, drugs, etc. into a patient's blood circulatory system.

BACKGROUND OF THE INVENTION

In general, the administration of transfusion is generally used for improving the general state of patients. In the most usual procedure, a cannula is inserted through the skin into a vein of the patient. The cannula is connected to a tube to supply the transfusible fluid which is administered for the patient in the prescribed amount for the proper length of time. To this end, various infusing systems have been proposed.

For example, Japanese U. M. publication No. 13858/83 discloses a conventional type plug device for a transfusion bottle which comprises a plug body of rubber adapted to be in liquid-tight sealed engagement with the mouth of the bottle. The rubber plug body is provided with a port for delivering the fluids and a port for passing an air into the bottle, and an elongated glass tube is connected to the air passing port and extends near the bottom of the bottle.

With such a conventional device, however, it is difficult to perfectly sterilize the inner portion of the elongated glass tube when the bottle is sterilized because the elongated glass tube has a relatively small diameter and a long length it also has disadvantages that the elongated glass tube may be easily broken, the plug device is bulky, and its construction is not sufficiently simple to alloW for easy handling. Further, it has a disadvantage that the fluids in the bottle may be easily contaminated by dust bacteria or other impurities prevailing in the air which is sucked up the glass tube and directly into the bottle in use.

In order to improve the aforementioned disadvantages, said Publication also discloses the provision of a water repellent but air permeable filter in the air passing port of the rubber plug body thereby resulting in that the elongated glass tube is not necessarily provided.

However, such a conventional arrangement has problems that since the plug body is directly contacted with the fluids, a component of the rubber which forms the plug body may be dissolved into the fluids during the storage and/or transportation of the transfusion fluid bottle ready for use.

There is also a tendency that air sucked into the bottle in use may be not actually flow upwardly, that is, toward the bottom of the bottle, but may short-circuitedly flow into an outlet tubing for connection to the patient. This means that it will exert a baneful influence upon the patient under medical treatment.

It is therefore an object of the present invention to provide a plug device for a transfusion container which can overcome the aforementioned problems involved in the conventional devices, and capable of protecting the fluids from any contamination which may be caused by dissolving of the rubber material of the plug body into the fluid during storage or transportation ready for use and or by the sucking in of an air in use and capable of preventing the sucked air from being short circuitedly introduced into a delivering port.

Another object of the present invention is to provide a plug device for a transfusion fluid container in which the plug device is formed integrally with a plastic container for containing the transfusion fluids.

SUMMARY OF THE INVENTION

According to the present invention, there is provided a plug device for a transfusion fluid container comprising a plug body made of rubber having a portion through which a hollow needle is inserted for delivering the fluid from the container and an air passing portion through which air is sucked into the container, said plug body being in liquid-tight sealed engagement with the mouth of said container, a water repellent but air-permeable filter which is forcedly inserted into said air passing portion, penetrable sealing sheet for covering at least the surface portion of said plug body which is contacted by the fluid contained in said container, and a funnel-shaped air guide which is formed integrally with the sealing sheet and the upper end of Which is extended toward the bottom of said container, said funnel-shaped air guide being arranged to guide the air sucked into said container through said filter toward the bottom of said container.

preferably, the container may comprise a bottle formed of glass or plastic material.

The sealing sheet and the funnel shaped air guide may preferably be formed of polypropylene, and may be welded to each other at their peripheral portions by using a high frequency induction welding.

Preferably, an outer sealing cap of a metal may be provided for holding the plug device in the mouth of the bottle, and this cap is partially removable and can be removed leaving the peripheral portion in use.

When the plug device is to be applied to the plastic bottle, the plug body may be wholly covered with the sealing sheet which in turn is integrally fixed on the mouth of the bottle by frequency induction welding.

The present invention will now be described by way of example with reference to the accompanying drawings:

DETAILED DESCRIPTION

Figure 1:
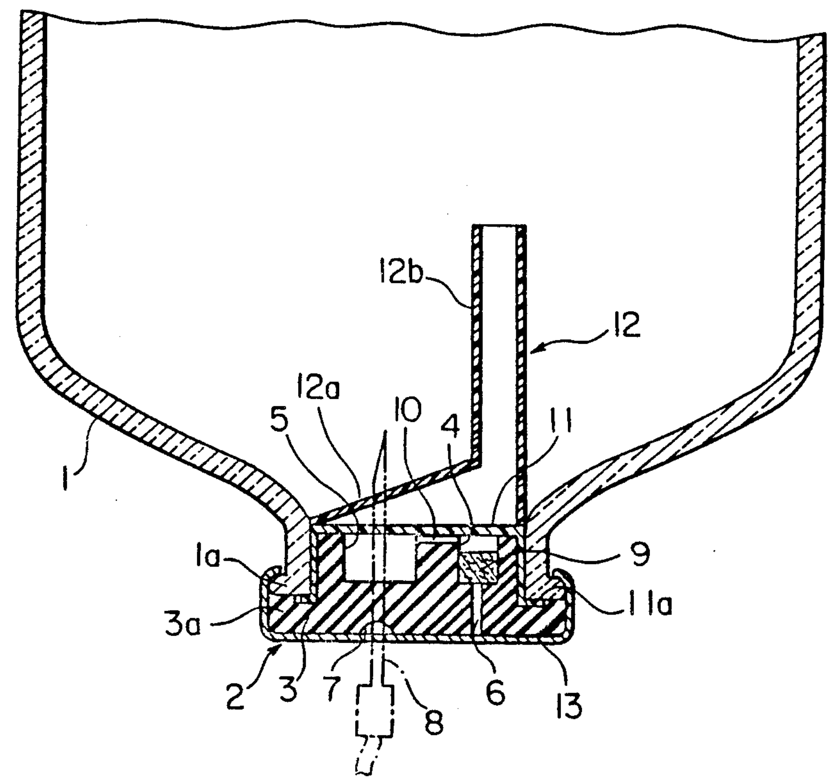
FIG. 1 is a schematic sectional view showing a plug device according to a first embodiment of the present invention which is applied to a glass bottle.
Figure 2:
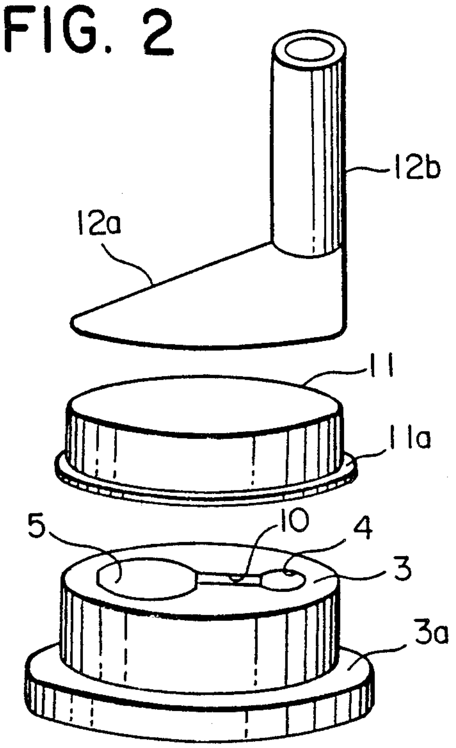
FIG. 2 is an exploded perspective view of the essential parts of the plug device of FIG. 1.

Reference is now made to FIGS. 1 and 2 of the drawings wherein an embodiment of the present invention is illustrated.

A container indicated generally by the reference numeral 1 comprises a generally flask-shaped glass bottle which contains transfusible fluids. The glass bottle 1 includes a mouth ia with which a plug device indicated generally by the reference numeral 2 is liquid-tightly engaged. The plug device 2 comprises a plug body 3 of rubber having a circular cross section, the flange 3*a* of which is in liquid-tight sealed engagement with the edge of the mouth 1*a*. The rubber plug body 3 is provided with holes 4 and 5 at the inner side thereof. The hole 4 leads to a slot 6 which is opened to the outer surface of the plug body 3. Opposite to the hole 5 is provided recesses (one of which is illustrated by reference numeral 7 in FIG. 1). Through these recesses and the hole 5 a hollow needle 8 is to be inserted for delivering the fluid from bottle I in use. If necessary, drugs may be injected into the transfusion fluid previously filled in the bottle 1 by inserting another hollow needle (not shown) through the recesses and the hole 5. Into the hole 4 is forcedly inserted a water repellent but air-permeable filter 9 of a fibrous material which passes only air into the bottle 1 but not dust, bacteria or other impurities. The hole 4 leads to the hole 5 by a groove 10.

The inner surface of the rubber plug body 3 is covered with a penetrable sealing sheet 11 made of polypropylene or membrane filter material, the circumferential portion 11*a* of which extends between the plug body 3 and the mouth 1*a* of the bottle 1 and is engaged with the edge portion of the mouth 1*a* of the bottle 1. On the sealing sheet 11 is integrally formed a funnel-shaped air guide 12 which includes a tubular extension 12*b* and an enlarged skirt 12*a* fixed to the circumferential portion 11*a* of sealing sheet 11 by means of high frequency induction welding. The tubular extension 12*b* is extended upwardly, that is, toward the bottom of the bottle 1. The tubular extension 12*b* is designed to have sufficiently large diameter so that the short-circuiting of the sucked air into the fluid delivering hollow needle 8 can be effectively prevented even if the length of the tubular, extension 12*b* is relatively short. This was experimentally assured.

The thus constructed plug assembly (3, 11 and 12) is tightly held in the mouth 1*a* of the bottle 1 by a sealing cap 13 of metal. In use, the sealing cap 13 can be partially removed, leaving the peripheral, portion so as to expose the slot 6 and the recesses 7.

In use, the bottle 1 filled with a suitable intravenous fluid is placed in a upright inverted position, and sealing cap 13 partially removed. The fluid delivering hollow needle 8 is then put through the rubber plug body 3, the sealing sheet 11 and the enlarged skirt 12*a* into the bottle 1 as shown in FIG. 1. Fluid begins to drip out of the inserted hollow needle 8, while air is sucked into the bottle i through the slot 6, the filter g in the hole 4, the groove 10, the hole 5 and the bore formed in the sealing sheet 11 by insertion of the needle 8. The air entering into the interior of the enlarged skirt 12*a* passes along the tubular extention 12*b* upwardly. In this case, although the enlarged skirt 12*a* is bored by insertion of the needle 8, the air entering into the interior of the enlarged skirt 12*a* does not substantially penetrate through the bore formed in the skirt 12*a* because the tubular extention 12*b* has sufficient cross section.

Figure 3:
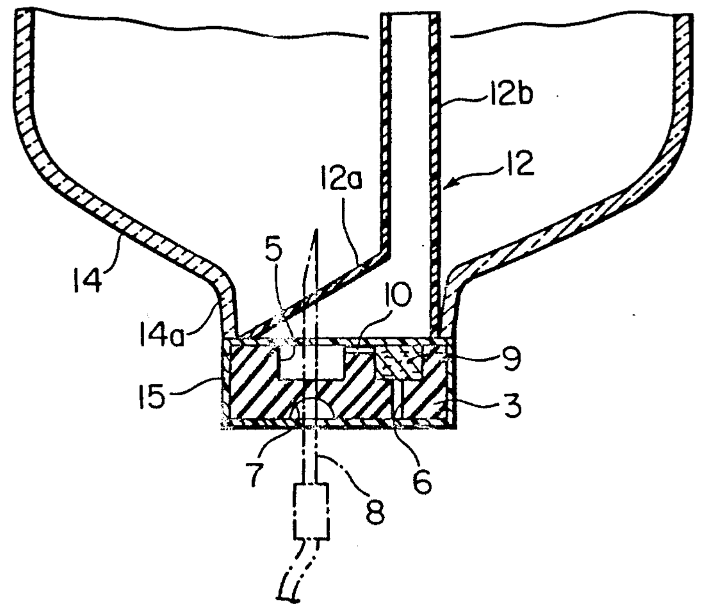
FIG. 3 is a schematic sectional view showing a second embodiment of the present invention Which is designed to use for a transfusion fluid bottle made of plastic material.

FIG. 3 shows a second embodiment of the present invention in Which the transfusion container comprises a generally flask shaped transparent plastic bottle 14, and the same components as those in the plug device of FIG. 1 are designated by the same reference numerals as those in FIG. 1.

In the embodiment shown in FIG. 3, the rubber plug body 3 is wholly covered with a sealing sheet 15 of polypropylene or membrane filter material, and is directly and sealingly secured on the edge of the mouth 14*a* of the plastic bottle 14.

Figure 4:
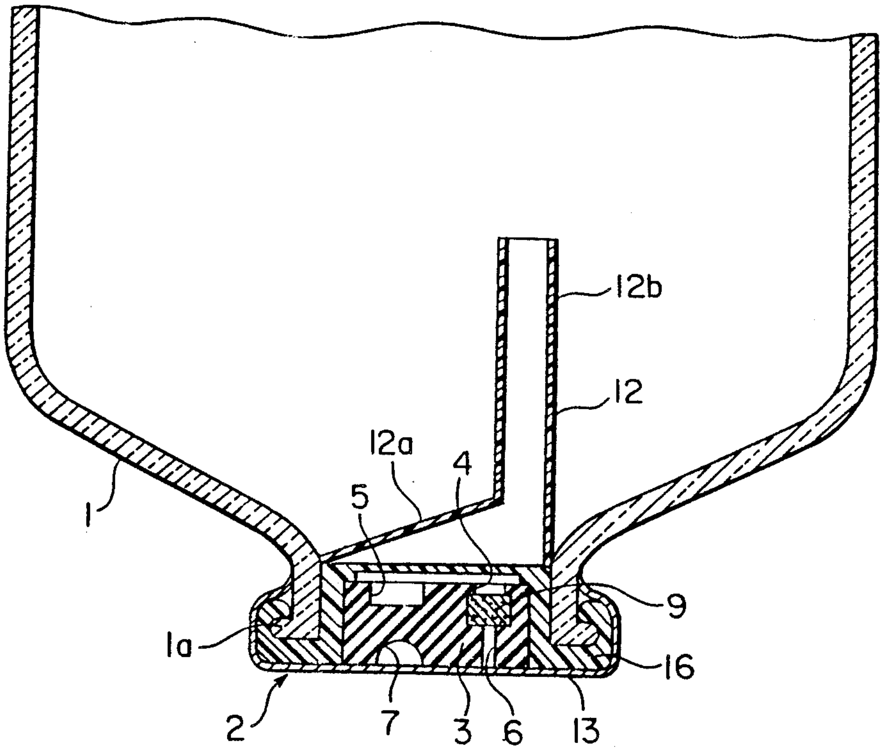
FIG. 4 is a schematic sectional view showing a third embodiment of the present invention.

FIG. 4 shows another embodiment of the present invention in which the rubber plug body 3 is a push-fit into an annular plug cap 16 of plastic material, and the same components as those in the plug device of FIG. 1 are designated by the same reference numerals as those in FIG. 1. The annular plug cap 16 is sealingly engaged with the edge of the mouth 1*a* of the glass bottle i, and may be formed integrally with the funnel-shaped air guide 12.

The pulg devices illustrated in FIGS. 3 and 4 may be operated in the same manner as that of FIG. 1.

According to the present invention as described above, since the sealing sheet is provided for covering at least the surface portion of the rubber plug body which may be contacted with the fluid in the container, it is possible to prevent the fluids from any contamination which may be caused by dissolving of the rubber material of the plug body during storage or transportation ready for use.

By the provision of the water repellent but airpermeable filter which is forcedly inserted into the air passing portion, any dropping out of the fluid through the air passing portion can be prevented and it is also possible to prevent dust, bacteria or other impurities from entering into the container.

The provision of the funnel-shaped air guide permits air flow toward the bottom of the container, thereby preventing the sucked air from being shortcircuitedly conducted into a delivering port.

The terms and expressions Which have been employed herein are used as terms of description and not of limitation, and there is no intention, in the use of such terms and expressions, of excluding any equivalents of the features shown and described but it is recognized that various modifications are possible within the scope of the invention claimed.

What is claimed is:

1. A plug device adapted to be in liquid-tight sealed engagement with the mouth of a transfusible fluid container, said plug device comprising: a plug body made of rubber having a needle insertion portion through which, in use, a hollow needle is inserted for delivering fluid from a container sealed by said plug device, and an air passing portion through which, in use, air is sucked into a container sealed by said plug device; a water repellent but air-permeable filter in said air passing portion; a sealing sheet covering at least the surface portion of said plug body which, in use, is contacted by intraveneous fluid contained in said container; and a funnel-shaped air guide having an enlarged skirt portion which is formed integrally with said sealing sheet and having a tubular extension the upper end of which, in use, extends toward the bottom of said container, said funnel-shaped air guide being arranged to guide air sucked through said air passing portion, in use, toward the bottom of said container.

2. A plug device as claimed in claim 1, wherein said sealing sheet and said funnel-shaped air guide are welded to each other at their peripheral portions.

3. A plug device as claimed in claim 1, wherein said hollow needle insertion portion includes an inner cavity and at least one outer recess provided on the outer surface of said rubber plug body.

4. A plug device as claimed in claim 1, wherein said air passing portion includes an inner cavity in which said water repellent but air-permeable filter is forcedly fitted and a slot, one end of said slot communicating with said inner hole and other end being opened to the outer surface of said rubber plug body.

5. A plug device as claimed in claim 1, wherein said rubber plug body is forcedly fitted into an annular plug cap of plastic material which is adapted to be sealingly engaged with the edge of a mouth of a container.

6. A plug device according to claim 1 wherein said hollow needle insertion portion comprises a cavity formed in said plug body, said needle insertion portion cavity being open to the inner surface of said plug body, wherein said air passing portion comprises a cavity in which said filter is located, said air passing portion cavity being open to the outer surface of said plug body, and wherein said plug body further comprises a passageway for the flow of air from said air passing portion cavity to said needle insertion portion cavity.

7. A plug device according to claim 6 wherein said passageway comprises a groove in the inner surface of said plug body.

8. A plug device according to claim 6 wherein the enlarged skirt portion of said funnel-shaped air guide, in use, is positioned directly above the needle insertion portion cavity whereby a needle inserted, in use, through said needle insertion portion will first penetrate said sealing sheet and then penetrate said skirt portion of said funnel-shaped air guide whereby, in use, air is free to flow from outside said plug into said air passing portion cavity, through said passageway, and into said needle insertion portion cavity.

9. A plug device adapted to be in liquid-tight sealed engagement with the mouth of a transfusible fluid container, said plug device comprising a plug body made of rubber having a portion through which, in use, a hollow needle is inserted for delivering fluid from a container sealed by said plug device, and an air-passing portion through which, in use, air is sucked into a container sealed by said plug device; a water repellent but air-permeable filter which is forcedly inserted into said air passing portion; a sealing sheet covering at least the surface portion of said plug body which, in use, is contacted by intraveneous fluid contained in said container; and a funnel-shaped air guide which is formed integrally with said sealing sheet and the upper end of which, in use, extends toward the bottom of said container, said funnel-shaped air guide being arranged to guide the air sucked into said container, in use, through said filter toward the bottom of said container, said sealing sheet and said funnel-shaped air guide being made of polypropylene, and being welded to each other at their peripheral portions by a high frequency induction welding.

10. A transfusible fluid container according to claim 9 further comprising an outer sealing cap of a metal for holding the plug device in the mouth of the bottle, said sealing cap being partially removable.

11. In a transfusible fluid container having a plug device in liquid tight sealing engagement with the mouth of the container, the improvement wherein the plug device comprises: a plug body made of rubber having a needle insertion portion through which, in use, a hollow needle is inserted for delivering fluid from a container sealed by said plug device and an air passing portion through which in use, air is sucked into said container; a water repellent but air-permeable filter in said air passing portion; a sealing sheet covering at least the surface portion of said plug body which, in use, is contacted by intraveneous fluid contained in said container; and a funnel-shaped air guide having an enlarged skirt portion which is formed integrally with said sealing sheet and having a tubular extension the upper end of which, in use, extends toward the bottom of said container, said funnel-shaped air guide being arranged to guide the air sucked through said air-passing portion, in use, toward the bottom of said container.

12. A transfusible fluid container according to claim 11 wherein said container comprises a plastic bottle and wherein said rubber plug body is wholly covered with said sealing sheet which in turn is integrally secured to the mouth of said plastic bottle.

13. A transfusible fluid container according to claim 11 wherein said sealing sheet and said funnel-shaped air guide are welded to each other at their peripheral portions.

14. A transfusible fluid container according to claim 11, wherein said hollow needle insertion portion includes an inner cavity and at least one outer recess provided on the outer surface of said rubber plug body.

15. A transfusible fluid container according to claim 11, wherein said air passing portion includes an inner cavity in which said water repellent but air-permeable filter is forcedly fitted and a slot, one end of said slot communicating with said inner hole and other end being opened to the outer surface of said rubber plug body.

16. A transfusible fluid container according to claim 11, wherein said rubber plug body is forcedly fitted into an annular plug cap of plastic material which is adapted to be sealingly engaged with the edge of the mouth of said container.

17. A transfusible fluid container according to claim 11 wherein said hollow needle insertion portion comprises a cavity formed in said plug body, said needle insertion portion cavity being open to the inner surface of said plug body, wherein said air passing portion comprises a cavity in which said filter is located, said air passing portion cavity being open to the outer surface of said plug body, and wherein said plug body further comprises a passageway for the flow of air from said air passing portion cavity to said needle insertion portion cavity.

18. A transfusible fluid container according to claim 17 wherein said passageway comprises a groove in the inner surface of said plug body.

19. A transfusible fluid container according to claim 17 wherein the enlarged skirt portion of said funnel-shaped air guide, in use, is positioned directly above the needle insertion portion cavity whereby a needle inserted, in use, through said needle insertion portion will first penetrate said sealing sheet and then penetrate said skirt portion of said funnel-shaped air guide whereby, in use, air is free to flow from outside said plug into said air passing portion cavity, through said passageway, and into said needle insertion portion passageway.

20. In a transfusible fluid container having a plug device in liquid tight sealing engagement with the mouth of the container, the improvement wherein said plug body comprises: a plug body made of rubber having a portion through which, in sue, a hollow needle is inserted for delivering fluid from a container sealed by said plug device, and an air-passing portion through which, in use, air is sucked into a container sealed by said plug device; a water repellent but air-permeable filter which is forcedly inserted into said air passing portion; a sealing sheet covering at least the surface portion of said plug body which, in use, is contacted by intraveneous fluid contained in said container; and a funnel-shaped air guide which is formed integrally with said sealing sheet and the upper end of which, in use, extends toward the bottom of said container, said funnel-shaped air guide being arranged to guide the air sucked into said container, in use, through said filter toward the bottom of said container, said sealing sheet and said funnel-shaped air guide being made of polypropylene, and being welded to each other at their peripheral portions by a high frequency induction welding.

* * * * *